United States Patent [19]

Duffett

[11] Patent Number: Plant 5,809

[45] Date of Patent: Nov. 25, 1986

[54] CHRYSANTHEMUM PLANT NAMED COMET

[75] Inventor: William E. Duffett, Salinas, Calif.

[73] Assignee: Yoder Brothers, Inc., Barberton, Ohio

[21] Appl. No.: 636,505

[22] Filed: Aug. 1, 1984

[51] Int. Cl.[4] ..... A01H 5/00

[52] U.S. Cl. ..... Plt./76

[58] Field of Search ..... Plt./76

*Primary Examiner*—R. E. Bagwill

*Attorney, Agent, or Firm*—Schwartz, Jeffery, Schwaab, Mack, Blumenthal & Evans

[57] ABSTRACT

A Chrysanthemum plant named Comet characterized as to uniqueness by the combined characteristics of tubular capitulum form, spider capitulum type, purple ray floret color; diameter across face of capitulum ranging from 7 to 9 cm. at maturity; uniform nine week flowering response, medium plant height when grown single stem, 15 to 25 cm. peduncles on open, normally terminal sprays, and 13° C. minimum temperature tolerance for initiation and development of flowering buds.

3 Drawing Figures

The present invention comprises a new and distinct cultivar of *Chrysanthemum morifolium,* Ramat., named Comet.

Comet is a product of a planned breeding program which had the objective of creating new Chrysanthemum cultivars having low temperature tolerance for cut spray mum programs, with spider capitulum type, purple ray floret color, nine week flowering response, and the ability to produce commercially acceptable quality in year round programs. Such traits in combination were not present or needed improvement in previously available commercial cultivars.

Comet, identified as 81757007, was originated from a cross made by William E. Duffett in a controlled breeding program in Salinas, Calif. in 1980. The female parent, identified as 781038002, was an unnamed purple decorative seedling. The male parent, identified as 79462001, was an unnamed purple decorative seedling.

Comet was discovered and selected as one flowering plant within the progeny of the stated cross by William E. Duffett on Nov. 6, 1981 in a controlled environment in Bogota, Colombia.

The first act of asexual reproduction of Comet as accomplished when vegetative cuttings were taken from the initial selection in January 1982 in a controlled environment in Bogota, Colombia by a technician working under formulations established and supervised by William E. Duffett through Fernando Jaramillo.

Horticultural examination of selected units initiated March 1983 has demonstrated that the combination of characteristics as herein disclosed for Comet are firmly fixed and are retained through successive generations of asexual reproduction.

Comet has not been observed under all possible environmental conditions. The phenotype may vary significantly with variations in environment such as temperature, light intensity, and day length. The following observations, measurements and comparisons describe plants grown in Bogota, Colombia under greenhouse conditions which approximate those generally used there in commercial practice.

The following traits have been repeatedly observed and are determined to be basic characteristics of Comet which in combination distinguish this Chrysanthemum as a new and distinct cultivar:

1. Tubular capitulum form.

2. Spider capitulum type.
3. Purple ray floret color.
4. Diameter across face of capitulum ranging from 7 to 9 cm. at maturity.
5. Uniform nine week photoperiodic flowering response to short days.
6. Long peduncle length, ranging from 15 to 25 cm.
7. Medium plant height, requiring two long day weeks prior to short days to attain a flowered plant height of 90 to 100 cm. for year around flowering.
8. Low temperature tolerance of 13° C. for initiation and development when grown in single stem cut spray programs with a continuous dark period of 12 hours.

The accompanying photographic drawings show typical inflorescence and leaf characteristics of Comet with the colors being as nearly true as possible with illustrations of this type.

Sheet 1 is a color photograph of Comet grown as a single stem cut spray.

Sheet 2 is a black and white photograph of three views of the inflorescence of Comet.

Sheet 3 is a black and white photograph showing the upper surface and under surface of leaves of Comet at three stages of development (mature, intermediate and immature).

Of the many commercial cultivars known to the present inventor, the most similar in comparison to Comet is Westland Pink, disclosed in U.S. Plant Pat. No. 4,589. Reference is made to attached Chart A which compares certain characteristics of Comet to those same characteristics of Westland Pink. Comet develops a deeper inflorescence color, longer peduncles, and larger capitulum diameter. The type, form, plant height, response and low temperature tolerance of Fantasy are similar to those same characteristics of Westland Pink.

In the following description, color references are made to The Royal Horticultural Society Colour Chart. The color values were determined on July 18, 1985 from plant material grown in Salinas, Calif.

Classification:

*Botanical.*—*Chrysanthemum morifolium,* Ramat., cv Comet.

*Commercial.*—Spider cut spray mum.

I. INFLORESCENCE

A. Capitulum:
*Form.*—Tubular.
*Type.*—Spider.
*Diameter across face.*—7 to 9 cm.

B. Corolla of ray florets:
*Color (general tonality from a distance of three meters).*—Purple.
*Color (upper surface of flat rays and inner surface of tubular rays).*—75A to 78C.
*Color (under surface of flat rays and outer surface of tubular rays).*—84C.
*Shape.*—Tubular outer rays and spoon inner rays.

C. Corolla of disc florets:
*Color (mature).*—145A.
*Color (immature).*—144B.

D. Reproductive organs:
*Androecium.*—Present disc florets only; scant pollen.
*Gynoecium.*—Present both ray and disc florets.

II. PLANT

A. General appearance:
*Height.*—Medium; 90 to 100 cm. as a flowering plant from a rooted cutting, with fourteen long days for a year around flowering maintaining a minimum nightly 12 hour continuous dark period.

B. Foliage:
*Color (upper surface).*—137A.
*Color (under surface).*148B.
*Shape.*—Deeply, broadly lobed and deeply serrated.

CHART A

COMPARISON OF COMET AND WESTLAND PINK

| CULTIVAR | RAY FLORET COLOR | CAPITULUM FORM AND TYPE | SPRAY FORMATION |
|---|---|---|---|
| COMET | PURPLE | TUBULAR SPIDER | 15 to 25 cm. PEDUNCLES |
| WESTLAND PINK | PURPLE | TUBULAR SPIDER | 10 to 20 cm. PEDUNCLES |

| CULTIVAR | DIAMETER ACROSS FACE OF CAPITULUM | PLANT HEIGHT |
|---|---|---|
| COMET | 7 to 9 cm. | MEDIUM 90 to 100 cm. |
| WESTLAND PINK | 6 to 8 cm. | MEDIUM 90 to 100 cm. |

| CULTIVAR | FLOWERING RESPONSE PERIOD | LOW TEMPERATURE TOLERANCE |
|---|---|---|
| COMET | 9 WEEKS | 13° C. |
| WESTLAND PINK | 9 WEEKS | 13° C. |

I claim:

1. A new and distinct plant of *Chrysanthemum morifolium,* Ramat., named Comet as described and illustrated, and particularly characterized as to uniqueness by the combined characteristics of tubular capitulum form; spider capitulum type; purple ray floret color; diameter across face of capitulum ranging from 7 to 9 cm. at maturity; uniform nine week flowering response; medium plant height when grown single stem; 15 to 25 cm. peduncles on open, normally terminal sprays, and 13° C. minimum temperature tolerance for initiation and development of flowering buds.

* * * * *

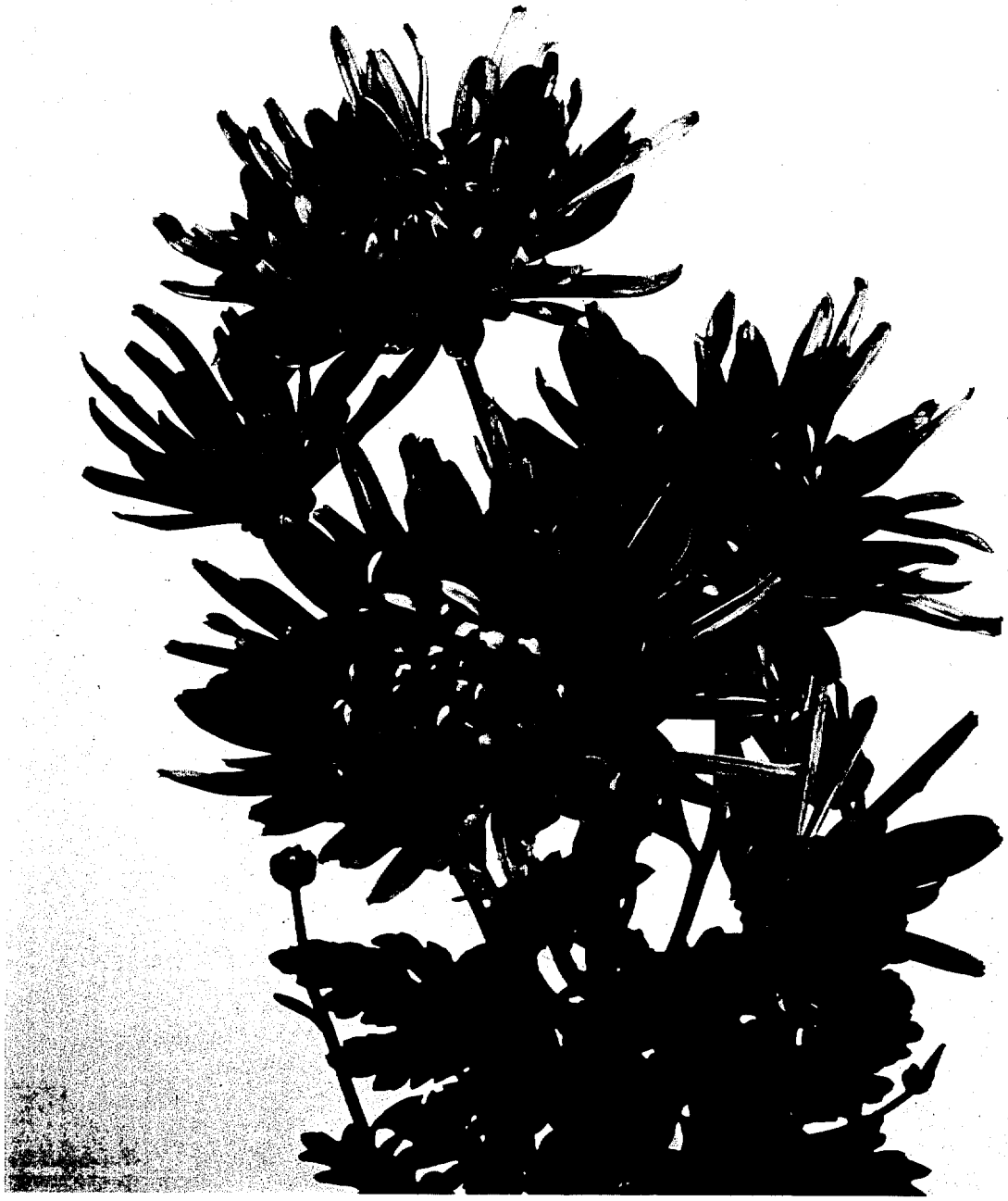

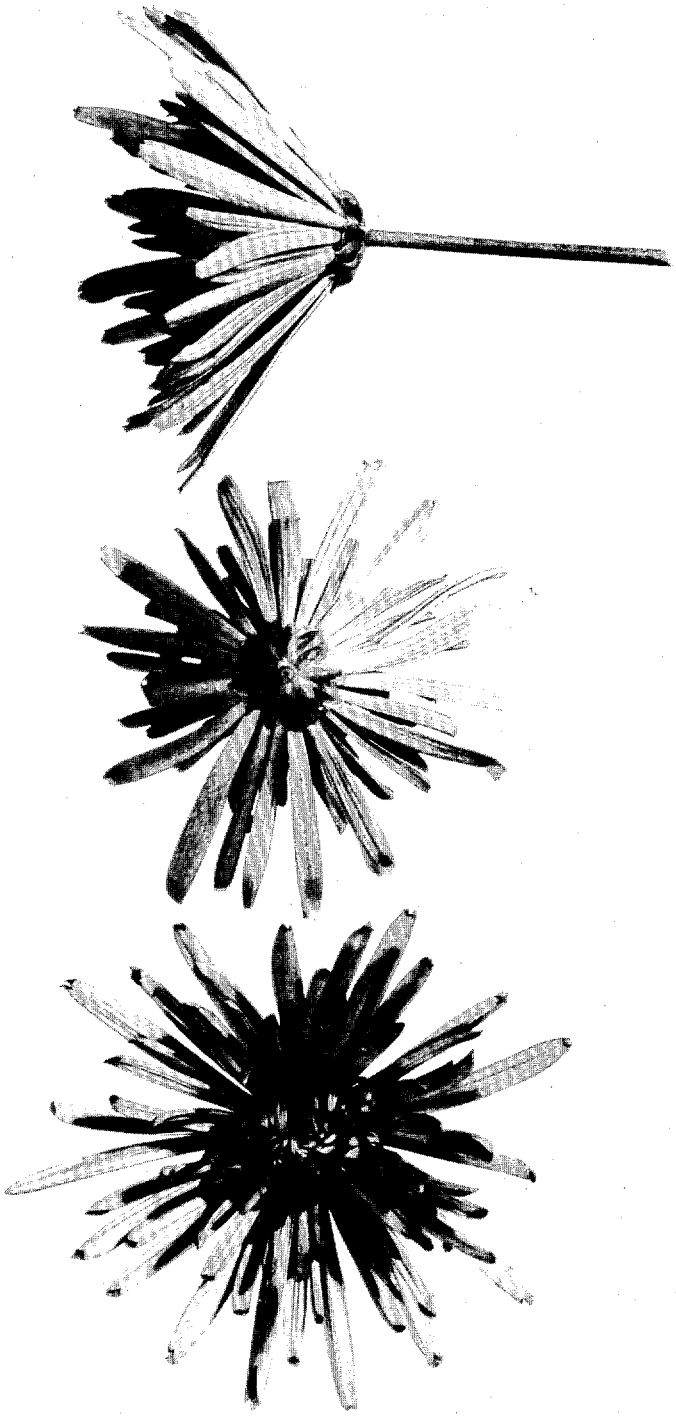

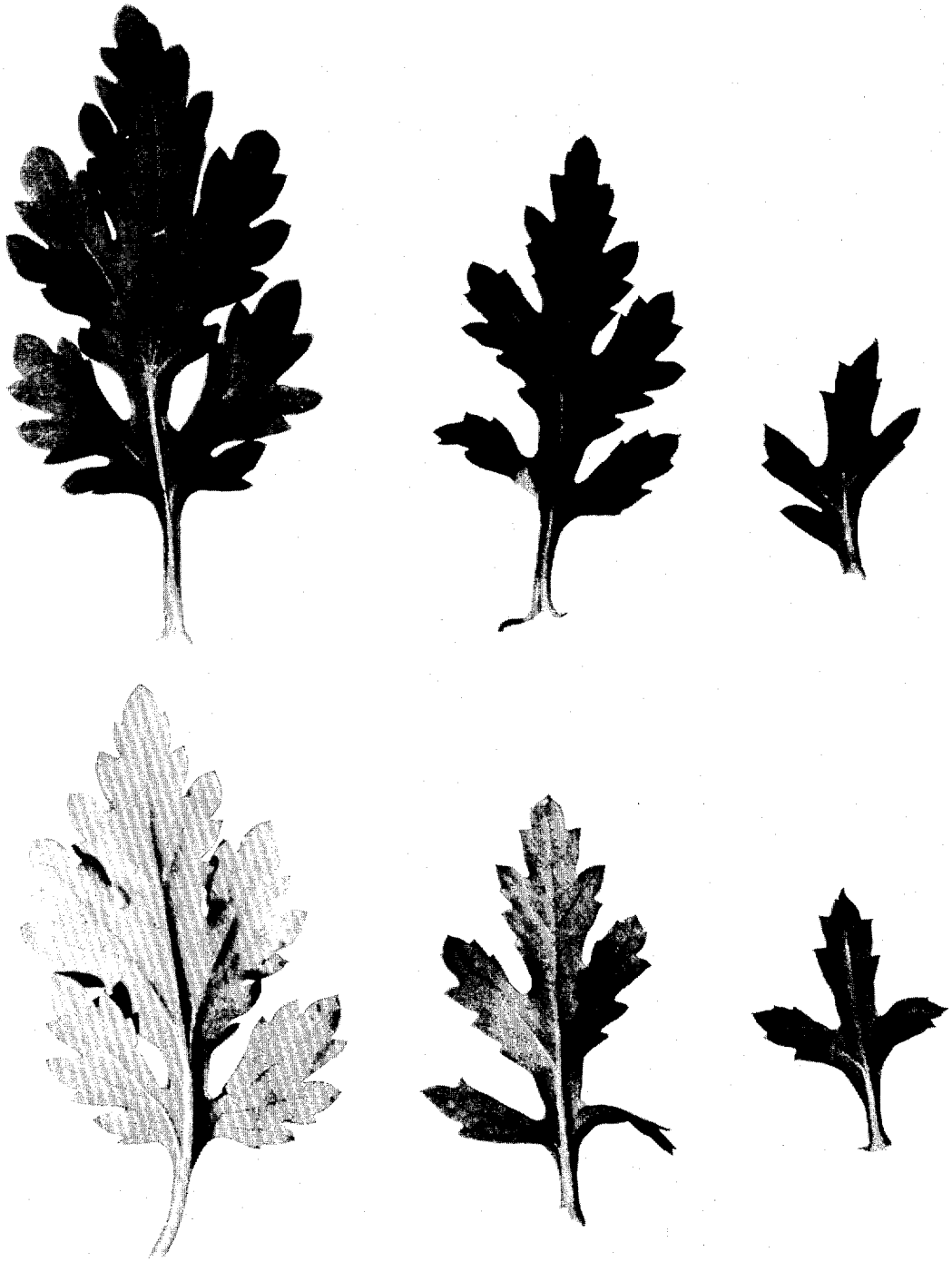

UNITED STATES PATENT AND TRADEMARK OFFICE

CERTIFICATE OF CORRECTION

PATENT NO. : PP05809

DATED : November 25, 1986

INVENTOR(S) : William E. Duffett

It is certified that error appears in the above-identified patent and that said Letters Patent is hereby corrected as shown below:

Column 1, line 23, change "as" to --was--.

Column 2, line 36, change "Fantasy" to --Comet--.

Signed and Sealed this

Twenty-eighth Day of April, 1987

*Attest:*

DONALD J. QUIGG

*Attesting Officer*

*Commissioner of Patents and Trademarks*